(12) United States Patent
Thacker

(10) Patent No.: US 6,622,042 B1
(45) Date of Patent: Sep. 16, 2003

(54) IMPLANTABLE CARDIAC STIMULATION DEVICE AND METHOD UTILIZING ELECTROGRAM SPECTRAL ANALYSIS FOR THERAPY ADMINISTRATION

(75) Inventor: James R. Thacker, Eureka, MO (US)

(73) Assignee: Pacesetter, Inc., Sylmar, CA (US)

( * ) Notice: Subject to any disclaimer, the term of this patent is extended or adjusted under 35 U.S.C. 154(b) by 248 days.

(21) Appl. No.: 09/852,884

(22) Filed: May 9, 2001

(51) Int. Cl.⁷ .............................................. A61N 1/365
(52) U.S. Cl. ......................................... 607/14; 600/518
(58) Field of Search ........................... 607/4–8, 14, 15; 600/515–518

(56) References Cited

U.S. PATENT DOCUMENTS

| | | | |
|---|---|---|---|
| 5,161,528 A | | 11/1992 | Sweeney ................. 128/419 D |
| 5,439,483 A | * | 8/1995 | Duong-Van ..................... 607/5 |
| 5,466,254 A | | 11/1995 | Helland ....................... 607/123 |
| 5,500,008 A | | 3/1996 | Fain .............................. 607/5 |
| 5,545,182 A | | 8/1996 | Stotts et al. .................... 607/5 |
| 5,578,062 A | | 11/1996 | Alt et al. ........................ 607/5 |
| 5,749,901 A | | 5/1998 | Bush et al. ..................... 607/5 |
| 5,792,189 A | | 8/1998 | Gray et al. ..................... 607/5 |
| 5,853,426 A | | 12/1998 | Shieh ............................. 607/5 |
| 6,292,694 B1 | * | 9/2001 | Schloss et al. ................. 607/9 |
| 6,438,410 B2 | * | 8/2002 | Hsu et al. .................... 600/516 |

OTHER PUBLICATIONS

Lindsay, Bruce D., MD, et al., "Noninvasive Detection of Patients with Ischemic and Nonischemic Heart Disease Prone to Ventricular Fibrillation", JACC vol. 16, No. 7, pp. 1656–1664, (Dec. 1990).

Kusuoka, Hideo, et al., "Calcuim Oscillations in Digitalis–Induced Ventricular Fibrillation: Pathogenetic Role and Metabolic Consequences in Isolated Ferret Hearts", Circulation Research, vol. 62, No. 3, pp. 609–619 (Mar. 1988).

Brown, Charles G., MD FACEP, et al., "Median Frequency–A New Parameter for Predicting Defibrillation Success Rate", Annals of Emergency Medicine, 20:7, pp. 787–789 (Jul. 1991).

Carlisle, Euan, J.F., MD M.R.C.P., et al., "Fourier Analysis of Ventricular Fibrillation and Synchronization of DC Coountershocks in Defibrillation", Journal of Electrocardiology, 21 (4), pp. 337–343, (1998).

Carlisle, E.J.F., et al., "Fourier Analysis of Ventricular Fibrillaiton for Varied Aetiology", European Heart Journal, 11, pp. 173–181, (1990).

Martin, Daniel R., et al., "Frequency Analysis of the Human and Swine Electrocardiogram During Ventricular Fibrillation", Resuscitation, 22, pp. 85–91 (1991).

Engel, Toby R., MD, "High–Frequency Electrocardiography: Diagnosis of Arrhythmia Risk", American Heart Journal, Progress in Cardiology, vol. 118, No. 6, pp. 1302–1316 (Dec. 1989).

* cited by examiner

Primary Examiner—Jeffrey R. Jastrzab

(57) ABSTRACT

An implantable cardiac stimulation device and method utilizes electrogram spectral analysis to administer electrical stimulation therapy to a heart to treat accelerated arrhythmias of the heart. The device includes an arrhythmia detector that initially detects an accelerated arrhythmia of the heart. An acquisition system then acquires an electrogram of the heart having both atrial and ventricular depolarization components. A processor then spectral analyzes the electrogram to provide spectral data related to the accelerated arrhythmia. The spectral data may be used for arrhythmia discrimination, arrhythmia tolerance discernment, and/or by a pulse generator to control stimulation therapy delivery timing.

24 Claims, 3 Drawing Sheets

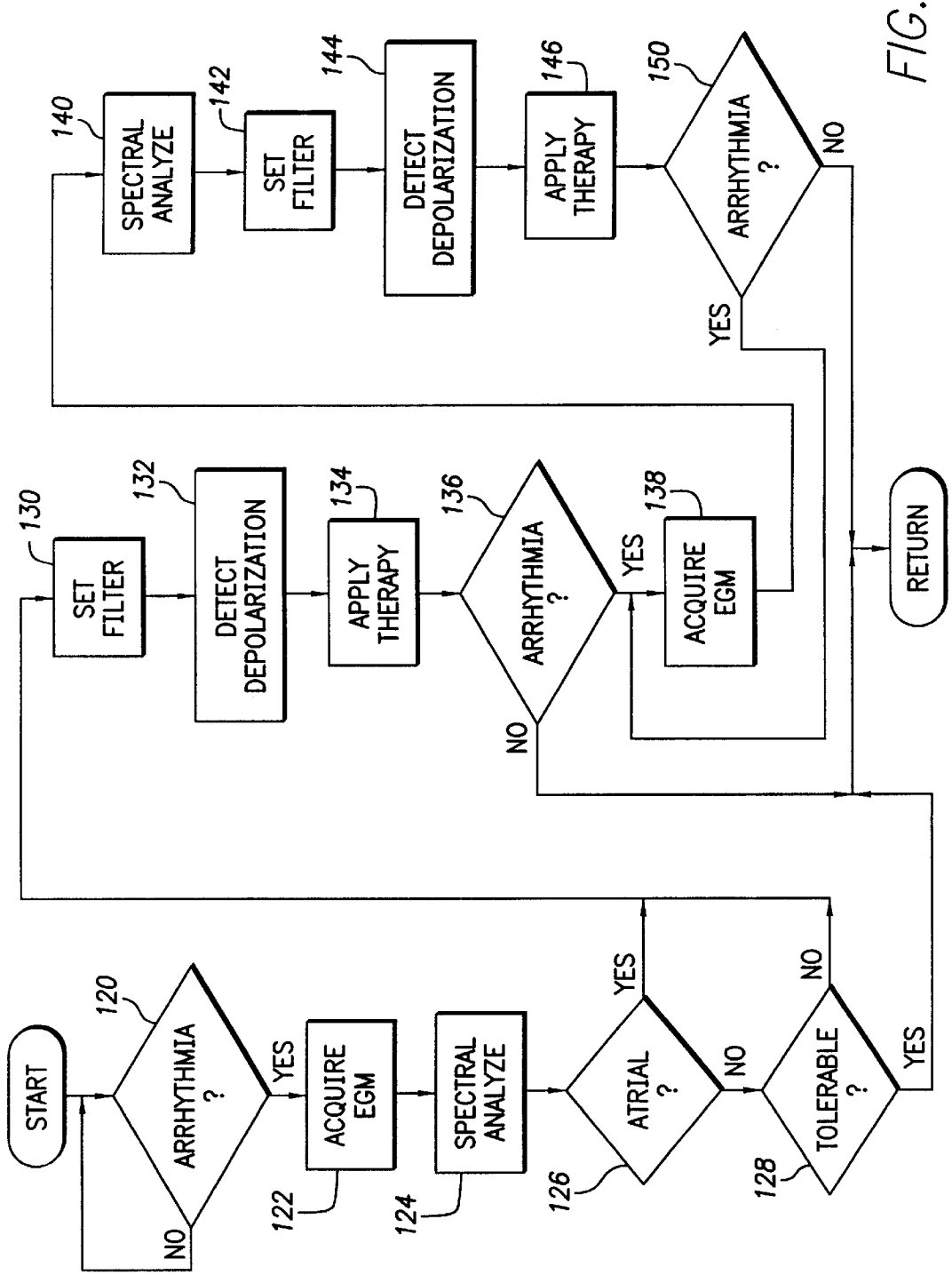

IMPLANTABLE CARDIAC STIMULATION DEVICE AND METHOD UTILIZING ELECTROGRAM SPECTRAL ANALYSIS FOR THERAPY ADMINISTRATION

FIELD OF THE INVENTION

The present invention generally relates to an implantable cardiac stimulation device. The present invention more particularly relates to such a device and a method utilizing spectral analysis of electrograms to administer arrhythmia therapy.

BACKGROUND OF THE INVENTION

Implantable cardiac stimulation devices are well known in the art. They include implantable pacemakers which provide stimulation pulses to a heart to cause a heart, which would normally or otherwise beat too slowly or at an irregular rate, to beat at a controlled normal rate. They also include defibrillators which detect when the atria and/or the ventricles of the heart are in fibrillation and apply cardioverting or defibrillating electrical energy to the heart to restore the heart to a normal rhythm. Implantable cardiac stimulation devices may also include the combined functionalities of a pacemaker and a defibrillator.

As is well known, implantable cardiac stimulation devices sense cardiac activity for monitoring the cardiac condition of the patient in which the device is implanted. By sensing the cardiac activity of the patient, the device is able to provide cardiac stimulation therapy when it is required.

One of the primary limitations of implantable cardiac devices is their size. Size limits body location of the implant and the number of patients capable of receiving the device. For these reasons, size has always been and continues to be a factor in distinguishing one device from another.

The size of an implantable cardiac device, especially those having defibrillation capability, is driven by two primary factors, the power or battery source and capacitors. Lower defibrillation thresholds will permit smaller sized batteries and capacitors in such devices. If the number of defibrillation shocks is kept constant, the total amount of required stored energy will be reduced if the amount of energy required for each shock is reduced. This permits a smaller battery to be used.

Capacitor size is influenced by voltage rating and capacitance value. Lower defibrillation thresholds permits employment of capacitors having lower voltage ratings and less capacitance and hence, smaller size. Reduced voltage rating also has other side benefits in circuit and component design.

The goal in delivering a defibrillation shock to a heart is to depolarize a sufficient number of myocardial cells to break the fibrillation wave cycles. Hence, if the defibrillation shock could be delivered at a time when the maximum number of myocardial cells are already intrinsically depolarized, a fewest number of cells are left remaining to be depolarized by the defibrillation shock to effect defibrillation. At this point in time, the defibrillator threshold will be at a minimum. Hence, it would be advantageous to be able to discern when the point of minimum threshold is occurring and then make practical use of it to lower defibrillation thresholds with the end result of being able to reduce the size of the battery and capacitors.

Still further, it would be advantageous to administer therapy of accelerated arrhythmias more effectively. For example, supraventricular arrhythmias and ventricular arrhythmias may be confused with one another. Each may exhibit similar symptoms such as increased and variable ventricular rates. Supraventricular arrhythmias require therapy to be applied to the atria while ventricular arrhythmias require therapy to be applied to the ventricles. Therapy applied to the incorrect chambers can be potentially dangerous to the patient and result in a waste of stored energy.

Still further, some ventricular arrhythmias may be tolerated by patients without the need of therapy intervention. For example, low rate ventricular tachyarrhythmias may not seriously compromise cardiac output and may even revert back to normal sinus rhythm on their own. Applying electrical therapy to such rhythms would represent needless use of energy and may cause a patient needless discomfort.

Hence, there is a need for effective management of accelerated rhythms. Such management should be capable of discriminating ventricular from supraventricular arrhythmias, discerning the need for therapy, and then applying therapy when the least amount of energy is required for successful treatment.

SUMMARY OF THE INVENTION

The present invention provides an implantable cardiac stimulation device and method which effectively manages accelerated arrhythmias. In accordance with the broader aspects of the present invention, electrogram spectral analysis is utilized for arrhythmia discrimination, tolerance discernment, and/or therapy delivery timing.

Arrhythmia discrimination is rendered possible because the physiology of the ventricles is different than the atria. For example, the ventricles are larger than the atria and the ventricular myocardium is thicker than the atrial myocardium. As a result, the distribution of the frequencies of depolarization for the ventricles is different than for the atria. A spectral analysis of an electrogram taken during an arrhythmic episode and having both atrial and ventricular components derived from, for example, a sensing electrode in or near one of the atria and a sensing electrode in or near one of the ventricles may thus be used to discriminate between a ventricular arrhythmia, requiring ventricular therapy and a supraventricular arrhythmia, requiring atrial therapy.

The frequency distribution of depolarization amplitude may also be used to determine if a ventricular arrhythmia is tolerable. This tolerance discernment of a tolerable ventricular tachyarrhythmia results in the withholding of unnecessary and energy consuming therapy.

If the arrhythmia is one requiring therapy, the frequency of maximum depolarization amplitude may be used for therapy delivery timing. When this frequency occurs, the maximum number of myocardial cells will already be depolarized leaving a minimum number of cells left to be depolarized by a defibrillation or cardioverting shock. The shock may be timed by setting a filter to the frequency of maximum depolarization amplitude. When the filter produces an output, the shock may be delivered. In some instances, the shock may be more effective if delayed with respect to the filter output. In either event, the therapy is delivered in timed relation to a depolarization having a frequency equal to the frequency of maximum depolarization.

In accordance with the present invention, an arrhythmia detector initially detects an accelerated arrhythmia of the heart. The initial determination may be based upon ventricular rate, ventricular rate and variability, or atrial rate. A data acquisition system provides an electrogram of the heart preferably including both atrial and ventricular depolarization components in response to the initial arrhythmia detection. The electrogram may be derived from a sensing electrode in the superior vena cava (SVC) and a sensing electrode in the right ventricle (RV) for example. The electrogram is then spectral analyzed to provide spectral data relating to the accelerated arrhythmia. The spectral data preferably includes depolarization amplitudes versus frequency. The spectral data is then used by a pulse generator that applies therapy responsive to the spectral data.

The chambers to receive therapy may be selected by the pulse generator based upon the frequency distribution of the depolarizations. The pulse generator may withhold therapy if the spectral data indicates the presence of a tolerable arrhythmia. Lastly, the pulse generator may time delivery of therapy to a frequency of maximum depolarization amplitude in order to effect a minimum cardioversion or defibrillation threshold.

BRIEF DESCRIPTION OF THE DRAWINGS

Further features and advantages of the present invention may be more readily understood by reference to the following description taken in conjunction with the accompanying drawings, in which:

FIG. 3 is a flow chart describing an overview of the operation of the preferred embodiment of the present invention.

DESCRIPTION OF THE PREFERRED EMBODIMENTS

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
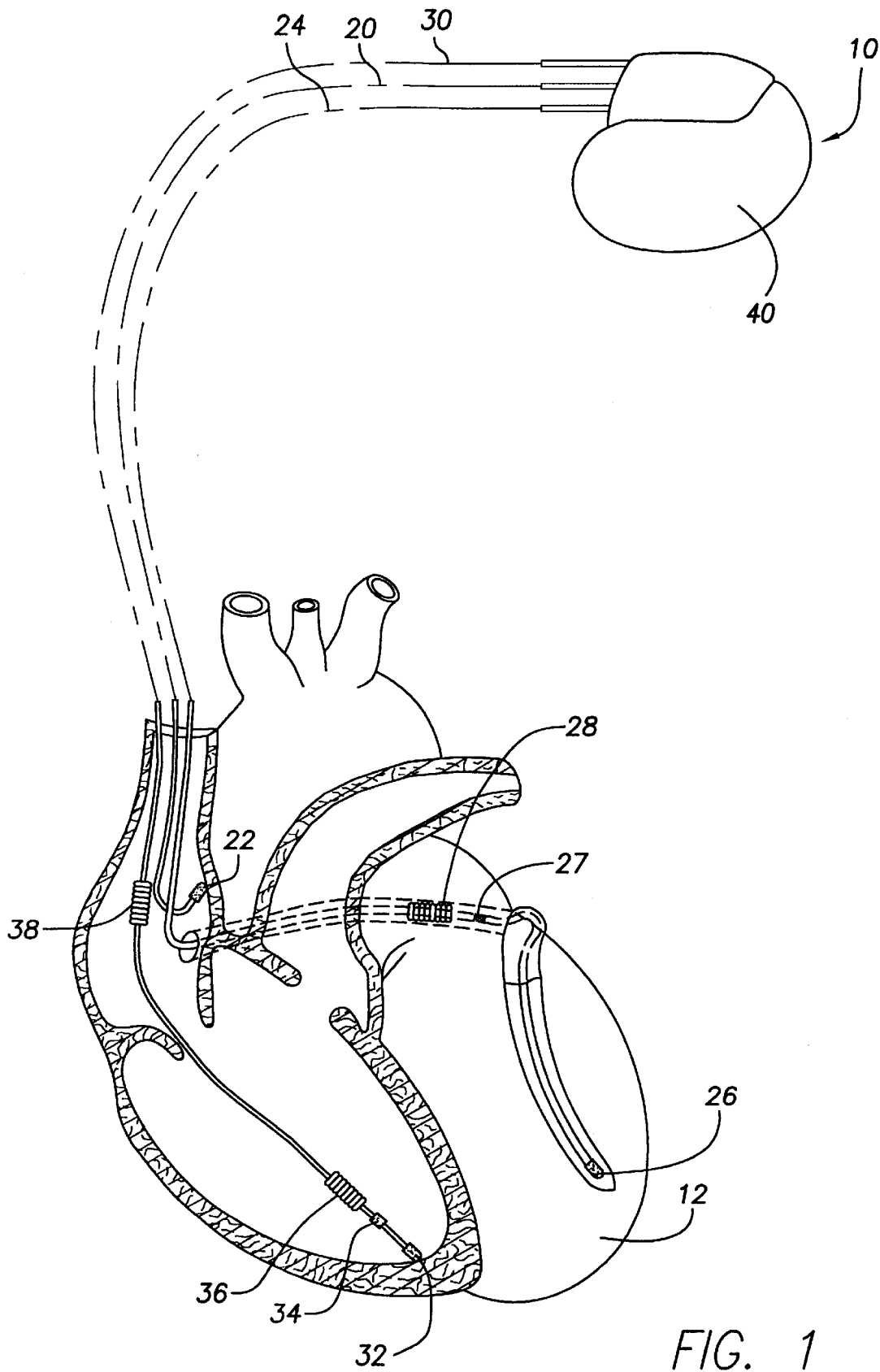
FIG. 1 is a simplified diagram illustrating an implantable stimulation device embodying the present invention in electrical communication with at least three leads implanted into a patient's heart for delivering multichamber stimulation and shock therapy.

As shown in FIG. 1, there is a stimulation device 10 in electrical communication with a patient's heart 12 by way of three leads, 20, 24 and 30 suitable for delivering multichamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left-chamber pacing therapy, the stimulation device 10 is coupled to a "coronary sinus" lead 24 designed for placement in the "coronary sinus region" via the coronary sinus os so as to place a distal electrode adjacent to the left ventricle and additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, the coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28. For a complete description of a coronary sinus lead, see U.S. patent application Ser. No. 09/457,277, "A Self-Anchoring, Steerable Coronary Sinus Lead" (Pianca et al.), and U.S. Pat. No. 5,466,254, "Coronary Sinus Lead with Atrial Sensing Capability" (Helland), which patents are hereby incorporated herein by reference.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
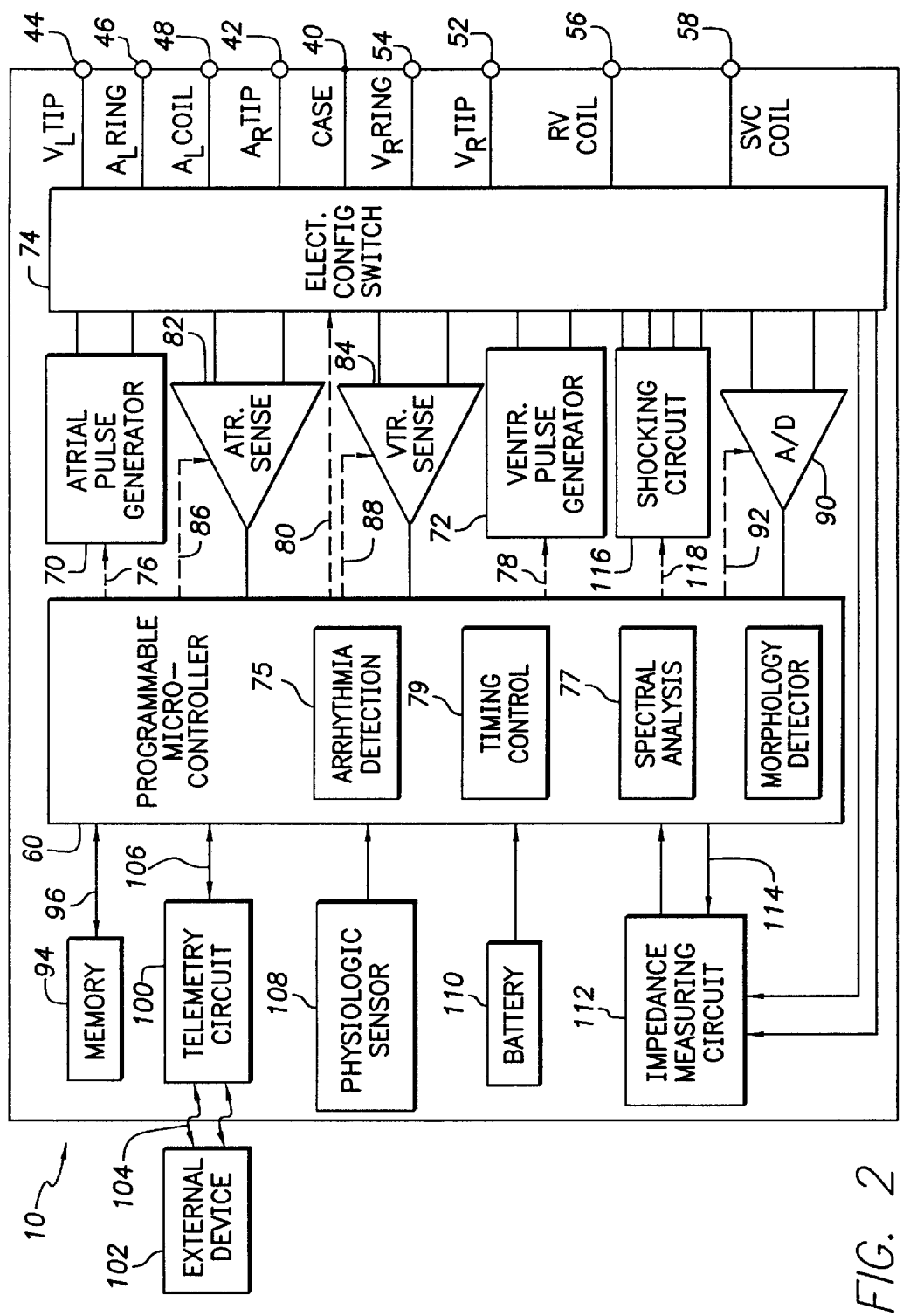
FIG. 2 is a functional block diagram of the device of FIG. 1 illustrating the basic elements of the device to provide cardioversion, defibrillation and pacing stimulation in four chambers of the heart as well as accelerated arrhythmia therapy management in accordance with a preferred embodiment.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal 42 adapted for connection to the atrial tip electrode 22.

To achieve left chamber sensing, pacing and shocking, the connector includes at least a left ventricular tip terminal 44, a left atrial ring terminal 46, and a left atrial shocking terminal 48, which are adapted for connection to the left ventricular tip electrode 26, the left atrial tip electrode 27, and the left atrial coil electrode 28, respectively.

To support right chamber sensing, pacing and shocking, the connector further includes a right ventricular tip terminal 52, a right ventricular ring terminal 54, a right ventricular shocking terminal 56, and an SVC shocking terminal 58, which are adapted for connection to the right ventricular tip electrode 32, right ventricular ring electrode, 34, the RV coil electrode 36, and the SVC coil electrode 38, respectively.

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via a switch bank 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing circuitry 79 which is used to control the timing of such stimulation pulses (e.g., pacing rate, atrio-ventricular (AV) delay, atrial interconduction (A—A) delay, or ventricular interconduction (V—V) delay, etc.) as well as to keep track of the timing of refractory periods, PVARP intervals, noise detection windows, evoked response windows, alert intervals, marker channel timing, etc., which is well known in the art.

The switch bank 74 includes a plurality of switches for connecting the desired electrodes to the appropriate I/O circuits, thereby providing complete electrode programmability. Accordingly, the switch bank 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch bank 74 for detecting the presence of cardiac activity in each of the four chambers of the heart. Accordingly, the atrial and ventricular sensing circuits, 82 and 84, may include dedicated sense amplifiers, multiplexed amplifiers, or shared amplifiers. The switch bank 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity, respectively, in the appropriate chambers of the heart. The sensing circuits, 82 and 84, in turn, receive control signals over signal lines, 86 and 88, from the microcontroller 60 for purposes of controlling the gain, threshold, polarization charge removal circuitry (not shown), and the timing of any blocking circuitry (not shown) coupled to the inputs of the sensing circuits, 82 and 86, as is known in the art.

The device 10 further includes arrhythmia detection 75 which provides initial accelerated arrhythmia detection and utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then compared to predefined rate zone limits for initial arrhythmia detection. Once an arrhythmia is detected, the spectral analysis 77 spectral analyzes an acquired electrogram (EGM) to provide spectral data. The spectral data is then used by the microcontroller 60 to determine the type of remedial arrhythmia therapy that is needed (e.g., anti-tachycardia pacing, cardioversion shocks or defibrillation shocks).

To support electrogram spectral analysis, cardiac signals are also applied to the inputs of an analog-to-digital (A/D) data acquisition system 90. The data acquisition system 90 is responsive to initial accelerated arrhythmia detection for acquiring at least one intracardiac electrogram signal, convert the raw analog signal into a digital signal, and store the digital signal for later spectral analysis and/or telemetric transmission to an external device 102. The electrogram signal preferably includes both atrial and ventricular components. The data acquisition system 90 is hence coupled to the SVC electrode 38, the atrial tip electrode 22, or the left atrial ring electrode 27, and the right ventricular tip electrode 32 through the switch bank 74 to sample a cardiac signal across both an atrium and a ventricle.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable device 10 may be non-invasively programmed into the memory 94 through a telemetry circuit 100 in telemetric communication with an external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through the established communication link 104.

In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V—V Delay, etc.) at which the atrial and ventricular pulse generators, 70 and 72, generate stimulation pulses.

The stimulation device additionally includes a battery 110 which provides operating power to all of the circuits shown in FIG. 2. For the stimulation device 10, which employs shocking therapy, the battery must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 employs lithium/silver vanadium oxide batteries, as is true for most (if not all) such devices to date.

As further shown in FIG. 2, the device 10 is shown as having an impedance measuring circuit 112 which is enabled by the microcontroller 60 by a control signal 114. The impedance measuring circuit 112 is not critical to the present invention and is shown for only completeness.

It is the primary function of the device 10 to function as an implantable cardioverter/defibrillator (ICD) device. That is, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 Joules), moderate (0.5–10 Joules), or high energy (11 to 40 Joules), as controlled by the microcontroller 60. Such shocking pulses are applied to the patient's heart through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as common).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 Joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

In FIG. 3, a flow chart is shown describing an overview of the operation and novel features implemented in one embodiment of the device 10 for managing accelerated arrhythmia therapy. In this flow chart, the various algorithmic steps are summarized in individual "blocks". Such blocks describe specific actions or decisions that must be made or carried out as the algorithm proceeds. Where a microcontroller (or equivalent) is employed, the flow charts presented herein provide the basis for a "control program" that may be used by such a microcontroller (or equivalent) to effectuate the desired control of the stimulation device. Those skilled in the art may readily write such a control program based on the flow charts and other descriptions presented herein.

The process of FIG. 3 initiates at a decision block 120 wherein the arrhythmia detector 75 decides if an accelerated arrhythmia is present. When an accelerated arrhythmia is initially detected in decision block 120 the process advances to activity block 122 for the acquisition of an electrogram to be spectral analyzed. Preferably, the electrogram is acquired with a pair of electrodes, one in or near an atrium and another in or near a ventricle for the generation of an electrogram signal having both atrial and ventricular depolarization components. For example, the electrodes used may include either the SVC electrode 38 or right atrial tip electrode 22 together with the right ventricular tip electrode 32. This permits later arrhythmia discrimination as well as tolerance discernment and therapy delivery timing. The electrogram signal is also preferably sampled at a fairly high rate, for example at a rate of 1000 Hz with appropriate low pass filtering prior to sampling. The electrogram signal is then digitized and stored in the memory 94.

After the electrogram is acquired, the process advances to activity block 124 wherein the stored electrogram is spectral analyzed. The spectral analysis may be performed in a manner known in the art to yield spectral data representing depolarization amplitude versus frequency.

Following the electrogram spectral analysis, the process proceeds to decision block 126 wherein arrhythmia discrimination is performed. Here, the microcontroller uses the spectral data to determine if the arrhythmia is a ventricular arrhythmia, requiring ventricular therapy, or a supraventricular arrhythmia, requiring atrial therapy. This discrimination is made possible, for example, by the ventricles being larger than the atria and the ventricular myocardium being thicker than the atrial myocardium. Hence, the depolarization amplitudes versus frequency of the ventricles will be different than that of the atria to permit the spectral data to be used for arrhythmia discrimination.

As an example, the depolarization amplitude versus frequency data resulting from electrogram spectral analysis during known episodes of ventricular and supraventricular arrhythmias may be prestored in the memory 94 as templates or signatures against which subsequent spectral data may be compared, as by template matching, for arrhythmia discrimination. Since the spectral morphology of ventricular and supraventricular arrhythmias are distinctly different, such discrimination may be made with accuracy.

As a further example, owing to the differences in physiology between the ventricles and the atria noted above, in many patients, the majority of depolarizations during ventricular arrhythmias will occur at lower frequencies than during supraventricular arrhythmias. Hence, during ventricular arrhythmias, the spectral data will be skewed toward lower frequencies and during supraventricular arrhythmia, the spectral data will be skewed toward higher frequencies. This difference alone in spectral morphology may be sufficient to support arrhythmia discrimination by spectral comparison.

As a still further example, for some patients, the majority of depolarizations during a ventricular arrhythmia may occur below a well defined given frequency. Hence, for these patients, the arrhythmia discrimination may be accomplished by the processor determining if the majority of depolarizations occur below or above the given frequency. If the majority of depolarizations occur below the given frequency, a ventricular arrhythmia may be declared to initiate ventricular therapy.

Conversely, if the majority of depolarizations occur above the given frequency, a supraventricular arrhythmia may be declared to initiate atrial therapy.

If it is determined in decision block 126 that the arrhythmia is ventricular, (not atrial or supraventricular) the process proceeds to decision block 128 to determine if the ventricular arrhythmia is one that is tolerable by the patient and hence one not in need of therapy delivery. Some ventricular arrhythmias, such as low rate ventricular tachycardias are tolerable and do not seriously compromise cardiac output. Such tolerable arrhythmias are characterized by a large maximum depolarization amplitude at a relatively low primary frequency. Hence, the spectral data may further be used to determine if the arrhythmia is tolerable and need not be treated. In this event, the process immediately returns. If however, the arrhythmia is atrial, as determined in decision block 126, or if the arrhythmia is a ventricular arrhythmia which is not tolerable, the process proceeds to activity block 130 to begin therapy delivery to the appropriate chambers of the heart.

In activity block 130, a digital filter, implemented by the microcontroller 60, is set to the frequency of maximum depolarization amplitude exhibited by the spectral data. At this depolarization frequency, the maximum number of myocardial cells will be intrinsically depolarized leaving a minimum number of cells left to be depolarized by a therapy shock to effect cardioversion or defibrillation. Hence, under this condition, the defibrillation threshold will be at a minimum.

Once the filter is set, the microcontroller advances to activity block 132 and waits for an output from the filter as the heart activity is sensed. When a depolarization is sensed at the frequency of maximum depolarization amplitude, the filter provides an output and the process advances to activity block 134 to apply the therapy shock in timed relation to the filter output. The delivery may be synchronized to the filter output or delayed with respect to the filter output. As will be seen hereinafter, if an initial synchronized therapy shock fails to successfully cardiovert the arrhythmia, the therapy delivery may be incrementally delayed on the next pass through.

After activity block 134, the process proceeds to decision block 136 for arrhythmia detector 75 to determine if the cardioversion or defibrillation attempt of activity block 134 was successful. If it was and there no longer is an arrhythmia, the process returns. However, if it was not successful, the process then advances to activity block 138 to acquire another electrogram for spectral analysis. Spectral analysis is preferably performed between cardioversion attempts since the prior attempts will have depolarized some myocardial tissue and hence may have changed the spectral data.

Following activity block 138, activity block 140 (spectral analysis), activity block 142 (set filter frequency), activity block 144 (detect depolarization), activity block 146 (apply therapy), and decision block 150 (arrhythmia detection) are performed cyclically in that order and as previously described until cardioversion of defibrillation is successful. Each time activity block 146 is reached, the therapy delivery may be delayed by an additional increment.

As will be appreciated by those skilled in the art, the spectral data signatures or distributions for arrhythmia discrimination and criteria for tolerance discernment may vary from patient to patient. Hence, these criteria may have to be learned over time for a given patient. In addition, to control therapy delivery time, methods other than a digital filter, may be used to this end. For example, template matching, known in the art, is one other technique which may be alternatively employed.

While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practice otherwise than as specifically described herein.

What is claimed is:

1. An implantable cardiac stimulation device that applies electrical stimulation therapy to a heart to treat accelerated arrhythmias of the heart, the device comprising:

an arrhythmia detector that detects an accelerated arrhythmia of the heart;

a sensor that provides an electrogram of the heart responsive to detection of an accelerated arrhythmia of the heart;

a processor that spectral analyzes the electrogram to provide spectral data related to the accelerated arrhythmia;

wherein the spectral data includes a frequency of maximum depolarization amplitude; and a pulse generator that administers electrical stimulation therapy to the heart responsive to the spectral data;

wherein the pulse generator applies electrical stimulation therapy to the heart in timed relation to a depolarization having a frequency equal to the frequency of maximum depolarization amplitude.

2. The device of claim 1 further including a memory that stores the electrogram prior to spectral analysis.

3. The device of claim 1 wherein the pulse generator applies the electrical stimulation therapy synchronized to the depolarization having a frequency equal to the frequency of maximum depolarization amplitude.

4. The device of claim 1 wherein the pulse generator applies the electrical stimulation therapy a delay time after the depolarization having a frequency equal to the frequency of maximum depolarization amplitude.

5. The device of claim 1 further including a filter tuned to the frequency of maximum depolarization that provides an output upon occurrence of the depolarization having the frequency of maximum depolarization.

6. An implantable cardiac stimulation device that applies electrical stimulation therapy to a heart to treat accelerated arrhythmias of the heart, the device comprising:

an arrhythmia detector that detects an accelerated arrhythmia of the heart;

a sensor that provides an electrogram of the heart responsive to detection of an accelerated arrhythmia of the heart;

a processor that spectral analyzes the electrogram to provide spectral data related to the accelerated arrhythmia; and a pulse generator that administers electrical stimulation therapy to the heart responsive to the spectral data;

wherein the processor is programmed to discriminate between a ventricular arrhythmia and a supraventricular arrhythmia responsive to the spectral data and to cause the pulse generator to administer the electrical stimulation therapy to a ventricle when the processor determines that a ventricular arrhythmia is present.

7. The device of claim 6 wherein the pulse generator administers the electrical stimulation therapy to an atrium when the processor determines that a supraventricular arrhythmia is present.

8. The device of claim 6 wherein the processor is programmed to determine if a ventricular arrhythmia is tolerable responsive to the spectral data and to cause the pulse generator to withhold administration of therapy when a ventricular arrhythmia is tolerable.

9. An implantable cardiac stimulation device for applying electrical stimulation therapy to a heart for treating accelerated arrhythmias of the heart, the device comprising:

arrhythmia detecting means for detecting an accelerated rhythm of the heart;

acquisition means for acquiring an electrogram of the heart responsive to the arrhythmia detecting means detecting an accelerated arrhythmia of the heart;

spectral analyzing means for performing spectral analysis of the acquired electrogram and providing spectral data related to the accelerated arrhythmia; and stimulation means for applying electrical stimulation therapy to the heart responsive to the spectral data;

wherein the stimulation means includes timing means for applying the electrical stimulation therapy to the heart in timed relation to a depolarization having a frequency equal to the frequency of maximum depolarization amplitude.

10. The device of claim 9 further including memory means for storing the acquired electrogram prior to spectral analysis.

11. The device of claim 9 wherein the timing means is adapted for applying the electrical stimulation therapy synchronized to the depolarization having a frequency equal to the frequency of maximum depolarization amplitude.

12. The device of claim 9 wherein the timing means is adapted for applying the electrical stimulation therapy a delay time after the depolarization having a frequency equal to the frequency of maximum depolarization amplitude.

13. The device of claim 9 wherein the timing means includes a filter tuned to the frequency of maximum depolarization for providing an output upon occurrence of the depolarization having the frequency of maximum depolarization.

14. An implantable cardiac stimulation device for applying electrical stimulation therapy to a heart for treating accelerated arrhythmias of the heart, the device comprising:

arrhythmia detecting means for detecting an accelerated rhythm of the heart;

acquisition means for acquiring an electrogram of the heart responsive to the arrhythmia detecting means detecting an accelerated arrhythmia of the heart;

spectral analyzing means for performing spectral analysis of the acquired electrogram and providing spectral data related to the accelerated arrhythmia;

stimulation means for applying electrical stimulation therapy to the heart responsive to the spectral data; and discrimination means for discriminating between a ventricular arrhythmia and a supraventricular arrhythmia responsive to the spectral data and causing the stimulation means to apply the electrical stimulation therapy to a ventricle when the discrimination means determines that a ventricular arrhythmia is present.

15. The device of claim 14 wherein the stimulation means applies the electrical stimulation therapy to an atrium responsive to the discrimination means determining that a supraventricular arrhythmia is present.

16. The device of claim 14 wherein the discrimination means includes means for determining if a ventricular arrhythmia is tolerable responsive to the spectral data for causing the stimulation means to withhold application of therapy when a ventricular arrhythmia is tolerable.

17. In an implantable cardiac stimulation device, a method of applying electrical stimulation therapy to a heart for treating accelerated arrhythmias of the heart, the method including the steps of:

detecting an accelerated rhythm of the heart;

acquiring an electrogram of the heart responsive to detecting an accelerated arrhythmia of the heart;

spectral analyzing the acquired electrogram and providing spectral data related to the accelerated arrhythmia, the spectral analyzing step including providing a frequency of maximum depolarization analysis; and applying electrical stimulation therapy to the heart responsive to the spectral data, the applying step including applying the electrical stimulation therapy to the heart in timed relation to a depolarization having a frequency equal to the frequency of maximum depolarization amplitude.

18. The method of claim 17 including the further step of storing the acquired electrogram prior to performing the spectral analysis.

19. The method of claim 17 wherein the apply step includes applying the electrical stimulation therapy synchronized to the depolarization having a frequency equal to the frequency of maximum depolarization amplitude.

20. The method of claim 17 wherein the applying step includes applying the electrical stimulation therapy a delay time after the depolarization having a frequency equal to the frequency of maximum depolarization amplitude.

21. The method of claim 17 wherein the applying step includes detecting an occurrence of the depolarization having the frequency of maximum depolarization.

22. In an implantable cardiac stimulation device, a method of applying electrical stimulation therapy to a heart for treating accelerated arrhythmias of the heart, the method including the steps of:

detecting an accelerated rhythm of the heart;

acquiring an electrogram of the heart responsive to detecting an accelerated arrhythmia of the heart;

spectral analyzing the acquired electrogram and providing spectral data related to the accelerated arrhythmia;

applying electrical stimulation therapy to the heart responsive to the spectral data; and discriminating between a ventricular arrhythmia and supraventricular arrhythmia responsive to the spectral data and wherein the applying step includes applying the electrical stimulation therapy to a ventricle when a ventricular arrhythmia is determined to be present.

23. The method of claim 22 wherein the applying step includes applying the electrical stimulation therapy to an atrium when a supraventricular arrhythmia is determined to be present.

24. The method of claim 22 including the further steps of determining if a ventricular arrhythmia is tolerable and withholding application of therapy when a ventricular arrhythmia is tolerable.

* * * * *